United States Patent [19]

Chan

[11] Patent Number: 4,567,279
[45] Date of Patent: Jan. 28, 1986

[54] DIARYLHYDROXY ALKANONES AND ALKENONES ANTIALLERGY AGENTS

[75] Inventor: Wan-kit Chan, Yorktown Heights, N.Y.

[73] Assignee: USV Pharmaceutical Corp., Tarrytown, N.Y.

[21] Appl. No.: 681,409

[22] Filed: Dec. 13, 1984

[51] Int. Cl.[4] ............... C07D 209/04; C07C 69/76; C07C 67/02
[52] U.S. Cl. ............... 548/491; 568/325; 568/331; 560/108; 560/255; 514/532; 514/543
[58] Field of Search ............... 548/491; 568/325, 331; 560/108, 255; 514/532, 543

[56] References Cited

U.S. PATENT DOCUMENTS

| 3,869,515 | 3/1975 | Trabor et al. | 568/325 |
| 3,950,427 | 4/1976 | Engel et al. | 568/325 |
| 4,064,269 | 12/1977 | Karrer | 568/325 |
| 4,218,468 | 8/1980 | Paul | 568/325 |
| 4,429,167 | 1/1984 | Lee | 568/325 |

FOREIGN PATENT DOCUMENTS 2501220  7/1976  Fed. Rep. of Germany ...... 568/325

Primary Examiner—Paul J. Killos

[57] ABSTRACT

This invention relates to new chemical compounds which possess valuable therapeutic activity particularly as lipoxygenase inhibitors possessing antiflammatory and antiallergic properties. The present new compounds are of the formula:

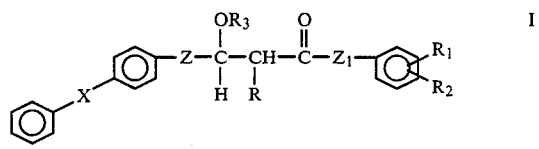

wherein,

Z and $Z_1$ each are alkylene chains containing up to three carbon atoms in the principal chain and a total of up to five carbon atoms and include from 0-1 double bonds;

R is H or lower alkyl;

$R_1$ and $R_2$ each are H, lower alkyl, OH, lower alkoxy, benzyloxy, carboxy, alkylenecarboxyl or alkylcarbonyl.

$R_3$ is H, lower alkyl, aralkyl or lower alkanoyl; and

X is $-O(CH_2)_n-$, $-CH=CH-$, $-(CH_2)_n-$, $-S(CH_2)_n-$ or

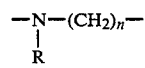

$n = 0$ or $1$
$n' = 1$ or $2$.

18 Claims, No Drawings

DIARYLHYDROXY ALKANONES AND ALKENONES ANTIALLERGY AGENTS

This invention relates to new chemical compounds which possess valuable therapeutic activity particularly as lipoxygenase inhibitors possessing anti-inflammatory and antiallergic properties. 3-[4-(4-chlorophenoxy)benzoylpropionic acid and phenoxyphenylalkanoic acids of the formula:

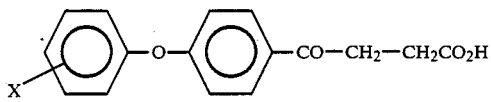

wherein, X=H, $CH_3$, $CH(CH_3)_2$, OH, $NHCOCH_3$, $COCH_3$, F, Cl, I and

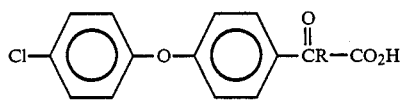

wherein,
R= —$CH_2$—, —$CH_2CO$—, —$CH_2CH(CH_3)$—, —$CH(CH_3)CH_2$—, —$CH(Me)CH(Me)$—, —$CH_2C(Me)_2$—,

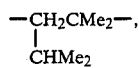

$(CH_2)_3$, —$(CH_2)_6$—, —HC=CH— (cis and trans), cyclopropyl (cis and trans), —$CH_2$—$C(CH_2)_5$—, and

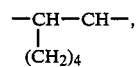

are described in Arzneim-Forsch/Drug Research 30(1) No. 3 (1980), pp. 454–458 as antihyperlipidemic agents In British Specification No. 1,390,580 are described therapeutic compounds of the formula:

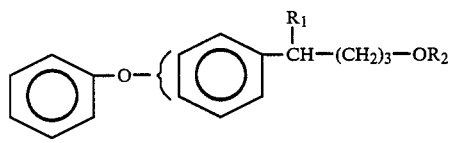

where,
$R_1$=H,

OH, alkoxy (1–6),
$R_2$=H, or acyl (mono or polycarboxylic acid of 1–6 (cis) phenoxy is meta or para to side chain.
The present new compounds are the formula:

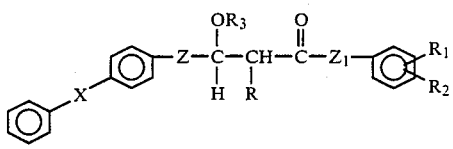

wherein,
Z and $Z_1$ each are alkylene chains containing up to three carbon atoms in the principal chain and a total of up to five carbon atoms and include from 0–1 double bonds;
R is H or lower alkyl;
$R_1$ and $R_2$ each are H, lower alkyl, OH, lower alkoxy, benzyloxy, carboxy, alkylenecarboxy or alkylcarbonyl.
$R_3$ is H, lower alkyl, aralkyl or lower alkanoyl; and X is —$O(CH_2)_n$—, —CH=CH—, or —$(CH_2)_{n'}$—, —$S(CH_2)_n$— or

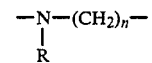

n=0 or 1  n'=1 or 2

The alkylene chains representative of each of Z and $Z_1$ contain up to three carbon atoms in the principal chain, i.e., in the normal configuration, and up to a total of 5 carbon atoms so that 1 or 2 angular methyl groups may be present on different or the same carbon atom, or an ethyl group on a single carbon atom. These chains may include a double bond, preferably in the α, ε position relative to the respective phenyl rings to which they are attached. The alkylene groups preferably contain two carbon atoms.

R is preferably hydrogen and $R_1$ and $R_2$ preferably are each hydroxy, lower alkoxy or benzyloxy, most preferably in the para and meta positions of the phenyl to which they are attached. $R_1$ and $R_2$ can also be other substituents such as halogen, phenoxy, mercapto, alkylthio, carboxy, carbalkoxy, carboxamide, nitrilo, sulfamyl, amino, mono and dialkylamino, formyl, trihalomethyl and nitro.

The unsubstituted phenyl groups depicted in formula I also be substituted with groups such as those recited for the substituents $R_1$ and $R_2$.

In the preferred compounds of this invention X is oxygen. Of course, X may also be —$S(CH_2)_n$— or

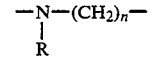

in which n=0 or 1.

Of the phenyl groups separated by X, each of these may be a heterocyclic ring containing at least one oxygen, sulfur or nitrogen including the so-called benzoheterocyclic rings. Exemplary heterocycles include thiophene, pyrrole, pyridine, thiazole, oxazole, benzofuran, quinoline, indole, benzothiophene, benzoxazole, and similar heterocyclic rings as well as the N-oxides of the nitrogen heterocyclics.

The alkyl groups, either alone or within the various substituents defined hereinbefore may be straight or branch chain and include methyl, ethyl, propyl, isopropyl, butyl, isobutyl, amyl, hexyl and the like.

The halo atoms in halo and trihalomethyl are Cl, Br, I and preferably F.

The present new compounds are prepared by known methods from starting materials either known or readily preparable.

The following general procedure can be employed.

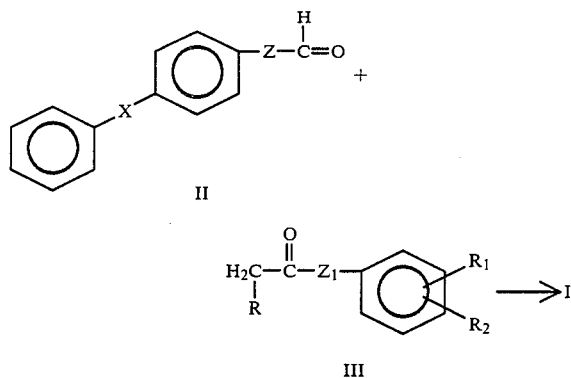

The substituents in formula II and III are as hereinbefore described.

The procedure is accomplished in the presence of an alkali metal or alkali metal-organic compound such as lithium dialkylamines, e.g., lithium diisopropylamine. Corresponding sodium or potassium compounds can also be used. The reaction is carried out in common solvents which are not reactive under the conditions employed, e.g., tetrahydrofuran, dioxane, dimethylformamide and equivalent solvents. During initial reaction the mixture is normally cooled to well below 0° C., e.g., down to −80° C., and preferably under a dry nitrogen atmosphere. Usually, the ketone of structure III is mixed with the alkali metal organic compound and thereafter the aldehyde of structure II is then added. After addition is complete, the reaction mixture under agitation is allowed to remain at the reaction temperature to assure completeness of reaction and then allowed to warm to room temperature. The product is then obtained by standard procedures of recovery.

It is desirable to employ blocking groups to protect substituents which may react during the course of the condensation reaction. For example, free hydroxy groups can be protected by the use of such blocking groups as trialkylsilyl groups which are readily removed on completion of the reaction. Alternatively, the hydroxy groups can be blocked by ether formation in the intermediate compounds prior to condensation employing alkyl groups or benzyl groups or by acylation with lower alkanoic acids. As desired, these blocking groups may be retained in the final product or removed, e.g. hydrogenolysis of the benzyl group.

It is possible to introduce further groups in the products thus obtained by standard organic synthetic methods such as acylation of free hydroxy groups, formation of ethers of free hydroxy groups as by Williamson Synthesis to alkoxy and benzyloxy compounds for example.

The compounds of the present invention can be administered to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained Preferred compositions or preparations according to the present invention are prepared so that an oral dosage unit form contains between about 50 and 300 mg of active compound The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent-such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions and dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

4-(4-Hexyloxyphenyl)-3-buten-2-one

To a solution of 4-hydroxybenzaldehyde (12 g, 0.1 M) in 250 ml of N,N-dimethylformamide (DMF) was added 20 g (0.12 M) of n-hexylbromide and 1 g of potassium carbonate. The mixture was heated at 60° C. for 6 hours.

After cooling down to room temperature, the solvent was removed under reduced pressure to give an oily residue. This substance was dissolved in 1 liter of acetone and 250 ml of water. Sodium hydroxide (5 g) was added and the mixture was stirred at room temperature for 48 hours. The bulk of solvent was removed on the rotary evaporator, the concentrated solution was acidified by 1 N aqueous hydrochloric acid and the product was extracted into diethyl ether. The etheral solution was washed with water, dried (magnesium sulfate) and concentrated on rotary evaporator to give an oily residue. Purification on a silica gel dry column (5% ethyl acetate in hexane) afforded 9.8 g of 4-(4-hexyloxyphenyl)-3-butene-2-one as an orange oil. Crystallization from ether-petroleum ether afforded yellow crystals, m.p. 55–57. MS(EI): 246 (m+).

EXAMPLE 2

4-(4-Hexyloxyohenyl)-butan-2-one

A mixture of 4-(4-hexyloxyphenyl)-3-buten-2-one (9.4 g, 38 mmol) and Raney Nickel ® (1 g of slurry in water, pH 10, Aldrich) in 200 ml of ethanol was shaken in a Parr hydrogenation apparatus at 40 psi for 2–4 hours. The mixture was then filtered through Celite ® and concentrated on rotary evaporator to give 9.4 g of the product as a pale yellow oil. MS(EI): 248 (m+); nmr (CDCl$_3$): 2.70 (t, J=7.5 Hz, 3); 3.87 (t, J=7.5 Hz, 3); 6.76 (d, J=7.5 Hz, 2); 7.05 (d, J=7.5 Hz, 2).

EXAMPLE 3

5-Hydroxy-1-(4-hydroxy-3-methoxyphenyl)-7-(4-phenoxyphenyl)heptan-3-one

A solution of lithium diisopropylamine, prepared from 4 ml of diisopropylamine and 14 ml of a 2.5 M solution of n-butyllithium, was stirred at −78° C. under a nitrogen atmosphere and a solution of 4-(3-methoxy-3-trimethylsilyloxyphenyl)-butan-2-one (4 g, 0.018 M) in 20 ml of dry tetrahydrofuran (THF) was added dropwise. The mixture was stirred for an additional 30 min. and a solution of 3-(4-phenoxyphenyl)-propan-1-al (4.6 g, 0.02 M) in 20 ml of THF was added dropwise. The mixture was stirred at −78° C. for 1 hr. After warming up to room temperature, 50 ml of ethyl acetate was added and the solution was washed with two 20 ml-portions of 10% hydrochloric acid and water. The crude product obtained after removal of solvent on a rotary evaporator was purified on a silica gel dry column (hexane: ethyl acetate, 2:1) to give 1.6 g of the product as a colorless oil. MS(EI): 420 (m+), 402 (m+-H$_2$O ).

EXAMPLE 4

5-Acetoxy-1-(4-acetoxy-3-methoxyphenyl)-7-(4-phenoxyphenyl)-heptan-3-one

A mixture of 5-hydroxy-1-(4-hydroxy-3-methoxyphenyl)-7-(4-phenoxyphenyl)-heptan-3-one (1.7 g, 4 mmol), acetyl chloride (0.6 ml, 8 mmol) and pyridine (1 ml) in 25 ml of THF was stirred at room temperature for 2 hours. Ethyl acetate (100 ml) was added and the mixture was washed with water, dried (magnesium sulfate) and concentrated on rotary evaporator to give an oily mixture. Purification by a silica gel dry column (hexane: ethyl acetate, 2:1) yielded 0.5 g of the product as a light yellow oil. MS(EI): 462 (m+-COCH$_2$ ), 444 (m+-CH$_3$CO$_2$H), 402 (m+-COCH$_2$-CH$_2$CO$_2$H).

EXAMPLE 5

5-Hydroxy-1-(4-hydroxy-3-methoxyohenyl)-7-(4-phenoxyphenyl)6-hepten-3-one

In a manner similar to Example 3, 3 g (0.012 M) of 4-(3-methoxy-3-trimethylsilyloxyphenyl)butan-2-one was reacted with 2.8 g (0.012 M) of 3-(4-phenoxyphenyl)-2-propen-1-al to give, after dry column purification (hexane: ethyl acetate, 2:1), 0.9 g of 5-hydroxy-1-(4-hydroxy-3-methoxyphenyl)-7-(4-phenoxyphenyl)-6-hepten-3-one as a pale yellow oil. MS(EI): 418.

EXAMPLE 6

5-Hydroxy-1-(4-hydroxy-3-methoxyohenyl)-7-(4-phenoxyphenyl)hepta-1,6-diene-3-one In a manner similar to Example 3, 2 g (9 mmol) of 4-(3-methoxy-4-trimethylsilyloxyphenyl-3-buten-2-one was treated with lithium diisopropylamine, followed by 2 g (9 mmol) of 3-(4-phenoxyphenyl)-2-propen-1-al. Purification of the crude product by dry column chormatography (silica gel, hexane: ethyl acetate, 2:1) gave 0.5 g of the desired product as a pale yellow oil. MS(EI): 398 (m+-H$_2$O).

EXAMPLE 7

7-(4-Benzyloxyphenyl)-5-hydroxy-1-(4-hydroxy-3-methoxyphenyl)-heptan-3-one

In a manner similar to Example 3, 2.2 g (10 mmol) of 4-(3-methoxy-4-trimethylsilyloxyphenyl)butan-2-one was treated with 10 mmol of lithium diisopropylamine, followed by 3 g (12 mmol) of 3-(4-benzyloxyphenyl)-propan-1-al. Purification of reaction mixture by dry column chromatography (silica gel, hexane: ethyl acetate, 2:1) gave 0.5 g of the desired product as a pale yellow oil. MS(EI):434.

EXAMPLE 8

7-(4-Benzyloxyphenyl)-1-(4-hexyloxyphenyl)-5-hydroxyheptan-3-one

In a manner similar to Example 3, 2.48 g (10 mmol) of 4-(4-hexyloxyphenyl)-butan-2-one was treated with 15 mmol of lithium diisopropylamine, followed by 3 g (12 mmol) of 3-(4-benzyloxyphenyl)-propan-1-al to give, after purification (silica gel dry column, hexane: ethyl acetate, 2:1), 0.7 g of the title compound pound as a pale yellow oil. MS(EI): 488 (m+), 470 (m+-$H_2O$) Using the method described hereinabove, the following examples further illustrate the invention:

5-Benzyloxy-1-(4-benzoyloxy-3-methoxyphenyl)7-(4-phenoxyphenyl)-heptan-3-one 1-(4-chloro-3-methoxyphenyl)-5-hydroxy-7-(4-phenoxyphenyl) heptan-3-one 1-(4-carboxyphenyl)-5-hydroxy-7-(4-phenoxyphenyl)-heptan-3-one 5-Benzyloxy-1-(4-chloro-3-methoxyphenyl)7-(4-phenoxyphenyl)-heptan-3-one 7-(1-Benzylindol-5--yl)-1-(4-chloro-3-methoxyphenyl)-5-hydroxyheptan-3-one The compounds of the present invention have potent activity in inhibition of lipoxygenease and phospholipase $A_2$ and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygeneases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484–486 (1980).

The following protocol describes an-assay to detect inhibitors of the lipoxygenase pathway. Such inhibitors are believed to be capable of modulating the biosynthesis of the leukotrienes, a property believed to be useful in treating asthma and inflammatory disease states.

Protocol for Detecting Inhibitors of the Lipoxygenase Pathway

A suspension of rat neutrophils in buffer is incubated for 3 minutes at 30° C. with [$^{14}C$]-arachidonic acid (AA) and Calcium Ionophore A23187. Citric acid (2M) is used to quench the reaction. Following the addition of a trace amount of ($^3H$)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, with are developed with an ethyl acetate/isooctane/water/acetic acid solvent system. The 5-HETE spots are visualized with iodine, cut out and placed in scintillation vials for counting. After adjusting for the extraction efficiency, the amount (pmole) of [$^{14}C$]5-HETE in each of the tubes in quantitated. The net pmoles of 5-HETE in the tubes containing buffer alone (blank) is subtracted from the pmoles of 5-HETE in the tubes containing buffer and cells (control). The ability of the test compounds to modulate the activity of this enzyme is determined by a decrease or increase in the net amount of 5-HETE produced.

Table I shows the concentration required for inhibition of the 5-lipoxygenase pathway (5-LOX/$I_{50}$ uM) for representative compounds according to the present invention.

TABLE I

| Compound of Example | LOX(RAT PMN); $I_{50}$(um) |
| --- | --- |
| 3 | 4.3 |
| 4 | 2.1 |
| 5 | 3.5 |
| 6 | 2.0 |
| 7 | 2.5 |
| 8 | 25 |

Inflammatory responses to a variety of offending stimuli are promoted by products of arachidonic acid metabolism. These products include leukotrienes (SRA-A), prostaglandins, prostacyclin and its metabolites, and thromboxanes. No matter what combination of products results from passage of substrate down the branches of this complex cascade, the initial step involves the release of arachidonic acid from phospholipids or from triglycerides containing this long-chain fatty-acid (1). The enzyme catalyzing such release of arachidonic acid are:

(a) phospholipase C followed by diglyceride lipase (2);

(b) phospholipase $A_2$, either soluble or membrane-bound (3,4); and (c) a lipase able to degrade triglycerides that contain arachidonic acid (1). The following protocol describes an assay to detect inhibitions of phospholipase $A_2$ enzyme. Such inhibitors are believed to be capable of modulating the biosynthesis of leukotrienes, a property believed to be useful in treating asthma and inflammatory disease states.

Protocol for detecting inhibitors of phospholipase $A_2$ enzyme

The $PLA_2$ employed in this screen is obtained by aggregation of purified rat platelets in the presence of $CaCl_2$ and ADP. In the enzyme assay phosphatidylcholine having $^{14}C$- labeled palmitate residues at R1 and R2 is employed as substrate. $PLA_2$ acts by cleaving the R2 fatty acid ester bond yielding free fatty acid and lysophosphatidyl choline as follows:

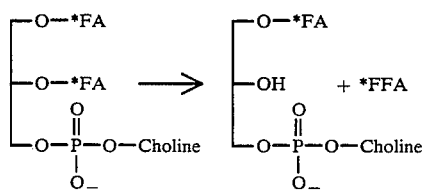

$^{14}C$—Phosphatidyl choline    $^{14}C$—Lysophosphatidyl choline    $^{14}C$—Palmitic acid Following completion of the reaction, the assay medium is acidified and extracted with hexane which takes up unreacted substrate and free fatty acid product. The hexane extract is passed over a short silica gel column which retains 99% of the phosphatidyl choline. The $^{14}C$-labeled palmitic acid is not retained (90% recovery in eluate) and is collected directly in scintillation counting vials. The released palmitic acid is conveniently quantitated by liquid scintillation spectrometry.

The compounds, were tested at 100 uM in a buffer containing 0.3 mM unlabeled phosphatidylcholine (PC), 20–30,000 cpm of $^{14}C[PC]$, 100mM NaCl, 1 mM $CaCl_2$ and 50 mM TRIS-HCl adjusted to pH 7.6 with 1 N NaOH. This resulted in a buffer pH of 7.2 at 37° C. The reaction was initiated by addition of the enzyme and it was terminated 30 minutes later by the addition of 100 ul of 1 N HCl.

Following acidification, the samples were extracted with 2 ml of 2-propanol plus 2 ml of hexane, vortexed, and allowed to stand until the phases separated. Free fatty acids (FFA) and some unreacted substrate are taken up in the isopropanol-saturated hexane. The hexane phase of the extraction mixture was transferred to a short silica gel column which retained unreacted PC but not the FFA. The column effluent was collected directly in scintillation vials. The columns were washed once with an additional 2 ml of hexane. The radiolabed FFA were quantitated by liquid scintillation spectrometry.

Table II shows the inhibitory activity of representative compounds according to the present invention.

TABLE II

| Compound of Example | $PLA_2$, $I_{50}$ (um) |
|---|---|
| 4 | 85* |
| 5 | 66 |
| 6 | 38 |
| 7 | 86* |
| 8 | 25 |

*Activity at buffer pH 9.0

These compounds of the present invention also display other activities as modulators of arachidonic acid metabolism; thus Example 5 inhibits cyclooxygenase ($I_{50}=12$ um) and Example 7 inhibits the synthesis of ukotrienes ($I_{50}=5$ um).

(REFERENCES)

1. Borgeat, P., M. Hamberg, and B. Samuelson. Transformation of arachidonic acid and homo-γ-linolenic acid by rabbit polymorphonuclear leukocytes. J. Biol. Chem., 251: 7816–7810 (1976).
2. Bell, R. L., D. A. Kennerly, N. Stanford, and P. W. Majerus. Diglyceride lipase: A pathway for arachidonate release from human platelets. Proc. Nat. Acad. Sci., U.S., 76: 3238–3241 (1979).
3. Vadas, P., and J. B. Hay. The release of phospholipase $A_2$ from aggregated platelets and stimulated macrophages of sheep. Life Sciences, 26: 1721–1729 (1980).
4. Franson, R. C., D. Eisen, R. Jesse, and C. Lanni. Inhibition of highly purified mammalian phospholipases $A_2$ by non-steroidal anti-inflammatory agents, modulation by calcium ions. Biochemical J., 186: 633–636 (1980).

What is claimed is:

1. A compound of the formula:

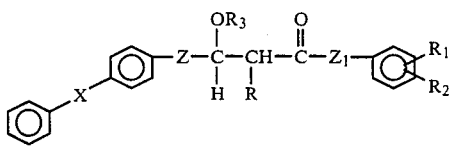

wherein,

Z and $Z_1$ each are alkylene chains containing up to three carbon atoms in the principal chain and a total of up to five carbon atoms and include from 0–1 double bonds;

R is H or lower alkyl;

$R_1$ and $R_2$ each are H, lower alkyl, OH, lower alkoxy, benzyloxy, carboxy, alkylenecarboxy or alkylcarbonyl;

$R_3$ is H, lower alkyl, aryl or lower alkanoyl; and

X is $-O(CH_2)_n-$, $-CH=CH-$, $-(CH_2)_{n'}-$, $-S(CH_2)_n-$ or

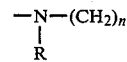

wherein n=0 and n'=1 or 2.

2. The compound according to claim 1 wherein each of Z and $Z_1$ contains two carbon atoms and R is H.
3. The compound according to claim 2 wherein X is $-O(CH_2)_n$ in which n=0 or 1.
4. The compound according to claim 2 wherein X is O.
5. The compound according to claim 4 wherein Z includes a double bond.
6. The compound according to claim 4 wherein each of Z and $Z_1$ includes a double bond.
7. 5-Hydroxy-1-(4-hydroxy-3-methoxyphenyl)-7-(4-phenoxyphenyl)-heptan-3-one.
8. 5-Acetoxy-1-(4-acetoxy-3-methoxyphenyl-)-7-(4-phenoxyphenyl)-heptan-3-one.
9. 5-Hydroxy-1-(4-hydroxy-3-methoxyphenyl)-7-(4-phenoxyphenyl)-6-heptan-3-one.
10. 5-Hydroxy-1-(4-hydroxy-3-methoxyphenyl)-7-(4-phenoxyphenyl)-hepta-1, 6-diene-3-one.
11. 7-(4-Benzyloxyphenyl)-5-hydroxy-1-(4-hydroxy-3-methoxyphenyl)-heptan-3-one.
12. 7-(4-Benzyloxyphenyl)-1-(4-hexyloxyphenyl)-5-hydroxy-heptan-3-one.
13. 5-Benzoyloxy-1-(4-benzoyloxy-3-methoxyphenyl)-7-(4-phenoxyphenyl)-heptan-3-one.
14. 1-(4-Chloro-3-methoxyphenyl)-5-hydroxy-7-(4-phenoxyphenyl)-heptan-3-one.
15. 1-(4-Carboxyphenyl)-5-hydroxy-7-(4-phenoxyphenyl)-heptan-3-one.
16. 5-Benzyloxy-1-(4-chloro-3-methoxyphenyl)-7-(4-phenoxyphenyl)-heptan-3-one.
17. 7-(1-Benzylindol-5-yl)-1-(4-chloro-3-methoxyphenyl)-5-hydroxyheptan-3-one.
18. A therapeutic composition comprising a compound according to claim 1 and a pharmaceutical carrier therefor.

* * * * *